United States Patent
Reddy et al.

(10) Patent No.: US 10,531,814 B2
(45) Date of Patent: Jan. 14, 2020

(54) METHOD AND APPARATUS FOR MOVING A REFERENCE DEVICE

(71) Applicant: Medtronic Navigation, Inc., Louisville, CO (US)

(72) Inventors: Robert J. Reddy, Broomfield, CO (US); Robert Teichman, Lafayette, CO (US)

(73) Assignee: Medtronic Navigation, Inc., Louisville, CO (US)

( * ) Notice: Subject to any disclaimer, the term of this patent is extended or adjusted under 35 U.S.C. 154(b) by 337 days.

(21) Appl. No.: 13/950,471

(22) Filed: Jul. 25, 2013

(65) Prior Publication Data

US 2015/0031985 A1    Jan. 29, 2015

(51) Int. Cl.
*A61B 5/06* (2006.01)
*A61B 90/00* (2016.01)
*A61B 34/20* (2016.01)

(52) U.S. Cl.
CPC .............. *A61B 5/061* (2013.01); *A61B 34/20* (2016.02); *A61B 90/39* (2016.02); *A61B 2090/364* (2016.02); *A61B 2090/3983* (2016.02)

(58) Field of Classification Search
None
See application file for complete search history.

(56) References Cited

U.S. PATENT DOCUMENTS

| | | | |
|---|---|---|---|
| 5,592,939 A | 1/1997 | Martinelli | |
| 5,740,808 A | 4/1998 | Panescu et al. | |
| 5,913,820 A | 6/1999 | Bladen et al. | |
| 6,381,485 B1 | 4/2002 | Hunter et al. | |
| 6,474,341 B1 | 11/2002 | Hunter et al. | |
| 6,533,455 B2 | 3/2003 | Graumann et al. | |
| 6,714,629 B2 | 3/2004 | Vilsmeier | |
| 7,570,791 B2 | 8/2009 | Frank et al. | |
| 7,751,865 B2 | 7/2010 | Jascob et al. | |
| RE42,226 E | 3/2011 | Foley et al. | |
| 8,126,535 B2 | 2/2012 | Maier et al. | |
| 8,350,730 B2 | 1/2013 | Siepmann | |
| 2004/0068263 A1 | 4/2004 | Chouinard et al. | |
| 2005/0215888 A1* | 9/2005 | Grimm | A61B 90/39 600/426 |
| 2005/0267358 A1* | 12/2005 | Tuma | A61B 90/39 600/414 |
| 2006/0094958 A1* | 5/2006 | Marquart | A61B 17/1662 600/434 |

(Continued)

FOREIGN PATENT DOCUMENTS

EP       1570802 A2    9/2005
WO   WO-2005104977 A1   11/2005

OTHER PUBLICATIONS

International Search Report and Written Opinion dated Oct. 8, 2014 for PCT/US2014/048031 claiming benefit of U.S. Appl. No. 13/950,471, filed Jul. 25, 2013.

(Continued)

*Primary Examiner* — Amelie R Gillman
(74) *Attorney, Agent, or Firm* — Harness Dickey and Pierce

(57) ABSTRACT

Disclosed is a method and system for navigating an instrument relative to a subject. A reference device can be associated with the subject. The reference device can be moved while maintaining or allowing registration with an image space.

23 Claims, 5 Drawing Sheets

(56) References Cited

U.S. PATENT DOCUMENTS

| | | | |
|---|---|---|---|
| 2008/0154125 A1* | 6/2008 | Maier | G06F 19/3437 |
| | | | 600/424 |
| 2008/0200808 A1 | 8/2008 | Leidel et al. | |
| 2009/0012509 A1* | 1/2009 | Csavoy | A61B 5/0059 |
| | | | 606/10 |
| 2009/0012532 A1* | 1/2009 | Quaid | A61B 17/1764 |
| | | | 606/130 |
| 2009/0093702 A1 | 4/2009 | Vollmer et al. | |
| 2010/0290690 A1* | 11/2010 | Hartmann | A61B 6/4405 |
| | | | 382/132 |
| 2010/0295931 A1 | 11/2010 | Schmidt | |
| 2011/0263971 A1 | 10/2011 | Nikou et al. | |
| 2013/0066196 A1 | 3/2013 | Graumann et al. | |
| 2014/0148808 A1* | 5/2014 | Inkpen | G01B 7/003 |
| | | | 606/80 |
| 2014/0330114 A1* | 11/2014 | Navab | A61B 1/041 |
| | | | 600/424 |

OTHER PUBLICATIONS

Internationall Preliminary Report on Patentability and Written Opinion dated Feb. 4, 2016 for PCT/US2014/048031 claiming benefit to U.S. Appl. No. 13/950,471, filed Jul. 25, 2013.
European Office Action dated Apr. 23, 2018 in corresponding European Application No. 14752477.1.
Office Action dated Feb. 25, 2019 in corresponding European Application No. 14752477.1.

\* cited by examiner

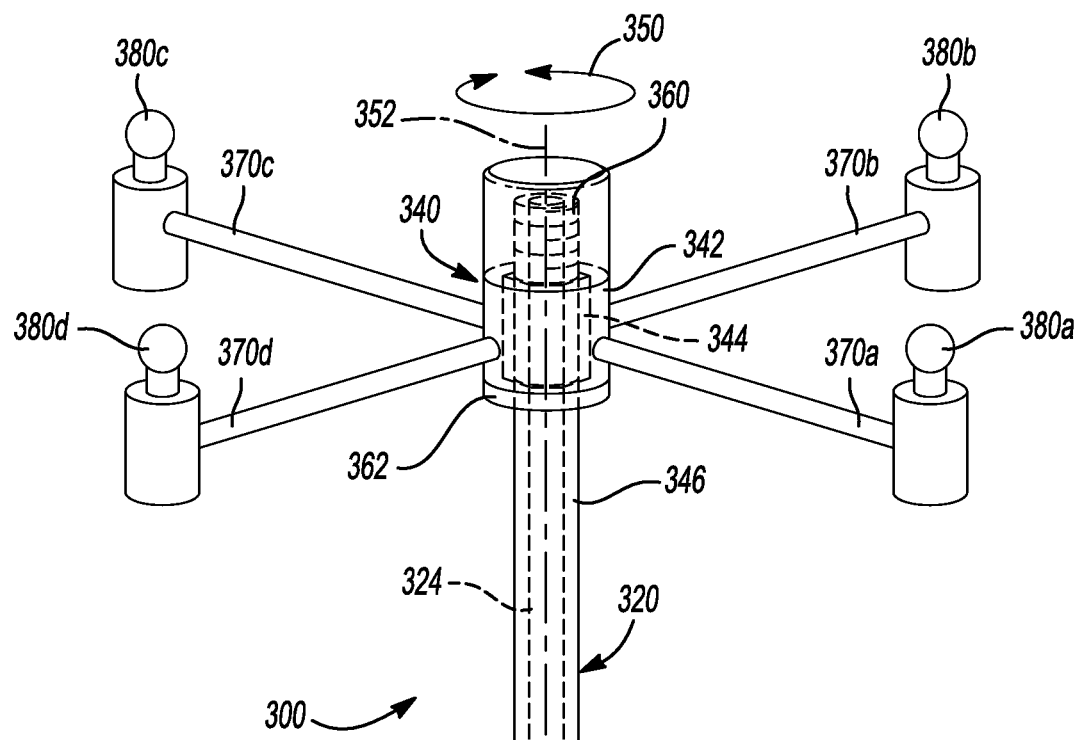
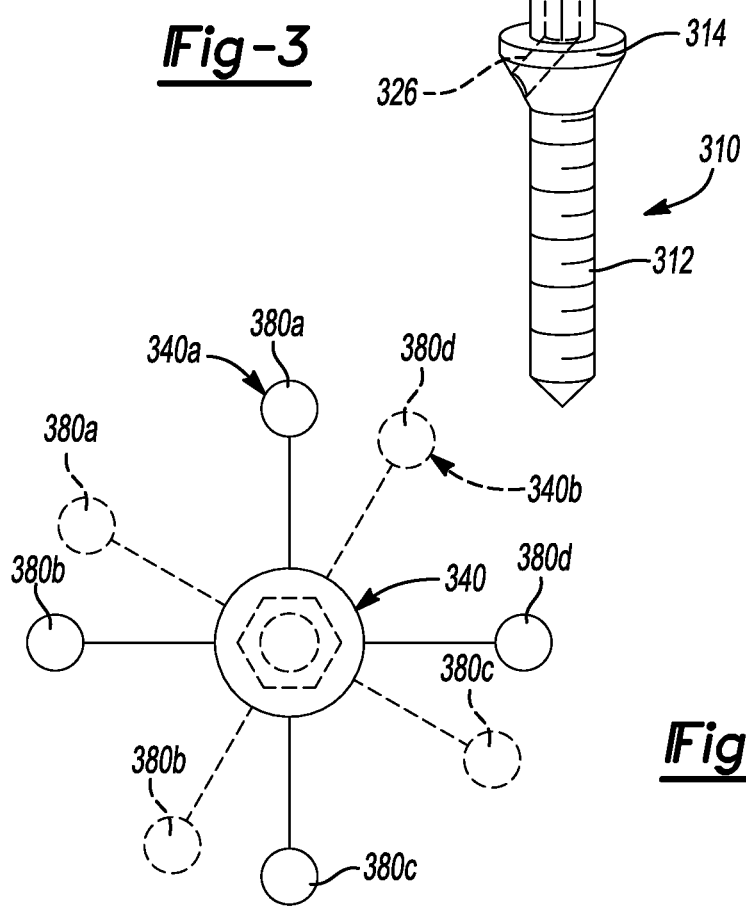
Fig-3
Fig-4

METHOD AND APPARATUS FOR MOVING A REFERENCE DEVICE

FIELD

The subject disclosure is related generally to a navigated procedure on a subject, and particularly to a navigated procedure on a subject with a reference device associated with a subject.

BACKGROUND

This section provides background information related to the present disclosure which is not necessarily prior art.

In performing a procedure, a user, such as a surgeon, can perform a procedure on a subject with a navigation system. The navigation system can assist in determining a location of a tracked device, such as a scalpel, catheter, or deep brain stimulation probe, by tracking a tracking device associated with the tracked device. The tracked device can include the instruments noted above, to which a tracking device is associated, such as directly affixed thereto. The instrument can allow a procedure to be performed on a subject while illustrating the location of the instrument relative to the subject. The position of the instrument can be illustrated relative to the subject by superimposing an icon representing the instrument on an image of the subject.

Image data is acquired of the subject for display prior to, during, and after a procedure on the subject. The image, including the image data which generates or is used to render the image, can be registered to the subject. The image data can define an image space that can include a three-dimensional space. The subject can likewise define a three-dimensional physical space to which the image data is registered. Registration can be performed in a plurality of processes.

According to various embodiments, a navigation system can use a selected tracking modality. The tracking system can include a localizer that generates or views the navigation field. For example, an optical tracking system can include one or more cameras as a localizer that views visible or infrared sources or reflectors. Alternatively, or in addition to an optical system, an electromagnetic navigation system (EM navigation system) can be used. In the EM system, one or more coils generates a field that is sensed by one or more sense coils to determine a location of an instrument.

SUMMARY

This section provides a general summary of the disclosure, and is not a comprehensive disclosure of its full scope or all of its features.

A navigation system can be used to assist in performing a procedure relative to a subject. The subject can include a living subject such as a human patient or a non-living subject. The navigation system can include a tracking system that tracks an instrument that is used in performing the procedure. The tracking system can include a patient tracker, also referred to as a dynamic reference frame, which can be used to track the patient.

During the navigated procedure the subject, which defines subject space, can be registered to image data, which defines image space. This allows a tracked location of the instrument to be illustrated on an image generated with the image data once registered. The dynamic reference frame allows the registration to be maintained even if the patient moves. A disclosed dynamic reference frame also allows the dynamic reference frame to be altered to a new determined and/or know location and/or position while maintaining the registration. Thus, the dynamic reference frame can be moved from a first position, at which a registration occurs, to a second position and a registration procedure need not be performed a second time. It is understood, as discussed further herein, that the dynamic reference frame, however, can be moved to any selected number of positions that are known and the registration may be maintained.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIG. 3 is a plan view of a dynamic reference frame, according to various embodiments;

FIG. 4 is a schematic view of an alterable position of the dynamic reference frame of FIG. 3;

Corresponding reference numerals indicate corresponding parts throughout the several views of the drawings.

DETAILED DESCRIPTION

Figure 1:
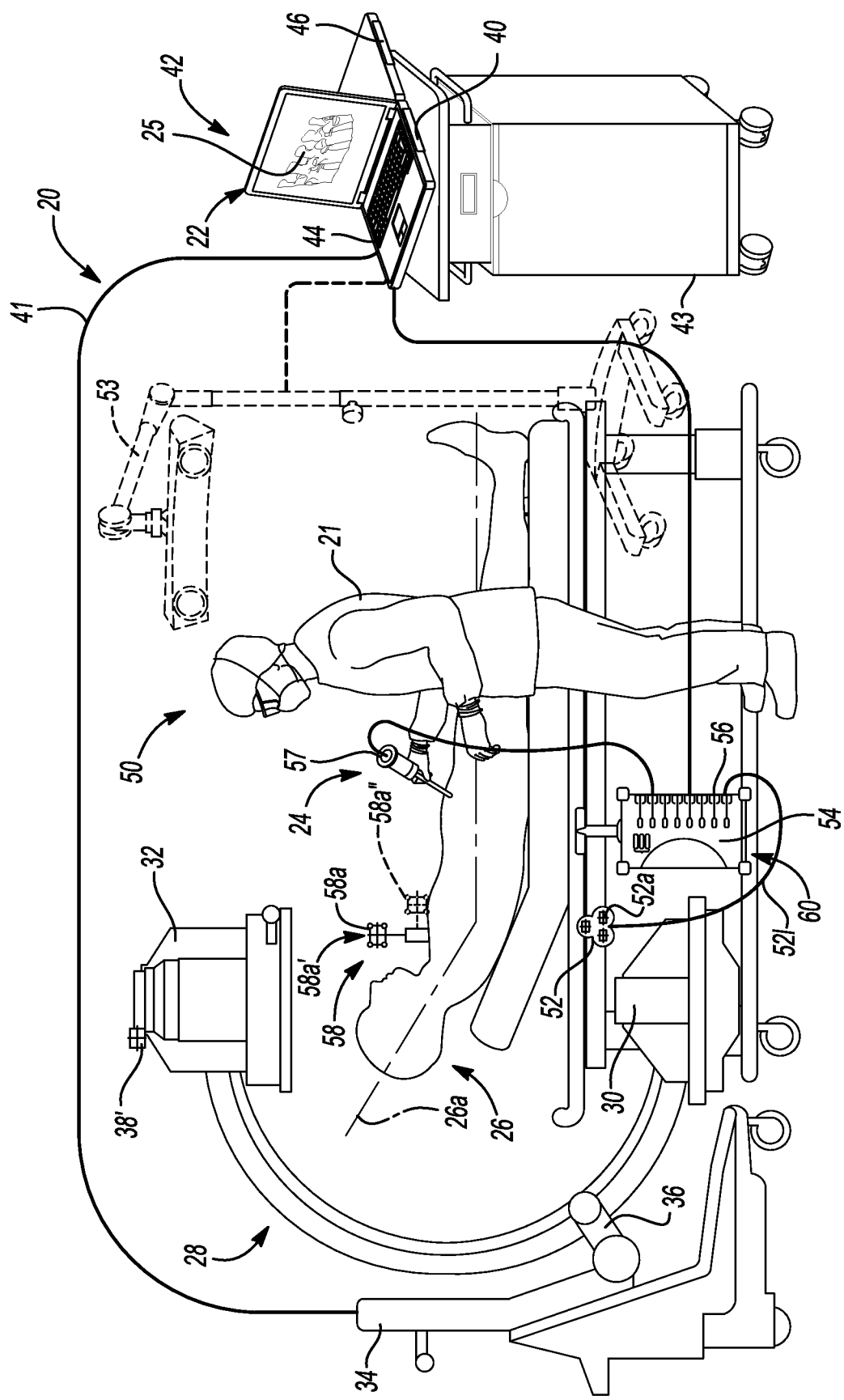
FIG. 1 is an environmental view of an operating room having a tracking system according to various embodiments.

Example embodiments will now be described more fully with reference to the accompanying drawings.

The following description is merely exemplary in nature and is not intended to limit the present disclosure, application, or uses. It should be understood that throughout the drawings, corresponding reference numerals indicate like or corresponding parts and features.

The present disclosure specifically provides an example of performing a procedure on a subject, such as a human patient. It is understood, however, that the subject invention is not limited to performing a procedure on only a patient. For example, a procedure can be performed on an animal subject as well. As a further alternative, the subject disclosure disclosing a device and a method can be performed relative to any appropriate volume. For example, a procedure can be performed relative to a volume, relative to a mechanical device or enclosed structure. The volume need not be of a living subject, but can be rather of an inanimate or animate object. In various examples the subject can be an object including an enclosed mechanical device. In various further examples, the subject can be a non-human animal A guided procedure can be performed with a navigation system 20, illustrated in FIG. 1. The guided procedure can be any appropriate procedure, such as a neurological procedure, cranial procedure, a spinal procedure, head (e.g.

sinus) procedures, cardiac procedure, oncology procedure, vascular procedure, an orthopedic procedure, or any appropriate procedure for which navigation may be used. The navigation system 20 can include various components, as will be discussed further herein. The navigation system 20 can allow a user, such as a surgeon 21, to view on a display device 22 a relative position of an instrument 24 relative to an image 25 of a subject 26 in a selected coordinate system. The position that is tracked can include a location in space and an orientation in space of the tracked device, including the instrument 24. The coordinate system can be made relative to the image 25, such as in an image guided procedure, or can be registered to a subject 26 only, such as in an imageless procedure. As noted above, the subject can be a human patient or any other appropriate subject.

Briefly, an imageless system can be provided which allows registration of the instrument 24 to subject space alone, rather than image space. In an imageless system, image data of the subject 26 need not be acquired at any time. Although image data can be acquired to confirm various locations of instruments or anatomical portions, such image data is not required. Further, the imageless system can be provided to allow for tracking the subject 26 and an instrument relative to the subject 26.

In an exemplary imageless system, a determination of a position of an anatomical structure can be made relative to the instrument and the locations of each can be tracked. For example, a plane of an acetabulum can be determined by touching several points with a tracked instrument (e.g. a tracked probe). A position of a femur can be determined in a like manner. The position of the relative portions, including the instrument and the anatomical portion, can be displayed on a display, with icons or graphics. The display, however, need not include image data acquired of the patient. One skilled in the art will understand that other data can be provided in an imageless system, however, like atlas data or morphed atlas data. The atlas data can be image data that is generated or generalized from a subject or a group of subjects. For example, a brain atlas can be generated based on detail analysis and study of image data of a brain of a selected patient. Nevertheless, an imageless system is merely exemplary and various types of imageless or image based systems can be used, including the image based system discussed below.

It should further be noted that the navigation system 20 can be used to navigate or track instruments, the instruments including: catheters, probes, needles, guidewires, instruments, implants, deep brain stimulators, electrical leads, etc. Moreover, the instrument can be used in any region of the body. The navigation system 20 and the various instruments 24 can be used in any appropriate procedure, such as one that is generally minimally invasive, arthroscopic, percutaneous, stereotactic, or an open procedure. Although an exemplary navigation system 20 can include an imaging device 28, one skilled in the art will understand that the discussion of the imaging device 28 is merely for clarity of the present discussion and any appropriate imaging system, navigation system, patient specific data, and non-patient specific data can be used. Image data can be captured or obtained at any appropriate time with any appropriate device.

The navigation system 20 can include the optional imaging device 28. The optional imaging device 28 or any appropriate imaging device can be used to acquire pre-, intra-, or post-operative or real-time image data of a patient 26. The illustrated imaging device 28 can be, for example, a fluoroscopic x-ray imaging device that may be configured as a C-arm 28 having an x-ray source 30 and an x-ray receiving section 32. Other imaging devices may be provided and reference herein to the C-arm 28 is not intended to limit the type of imaging device. As understood by one skilled in the art, an optional calibration, and/or tracking target 38', and optional radiation sensors can be provided. Image data may also be acquired using other imaging devices, such as those discussed herein. An example of a fluoroscopic C-arm x-ray device that may be used as the optional imaging device 28 is the "Series 9600 Mobile Digital Imaging System," from OEC Medical Systems, Inc., of Salt Lake City, Utah. Other exemplary fluoroscopes include bi-plane fluoroscopic systems, ceiling fluoroscopic systems, cath-lab fluoroscopic systems, fixed C-arm fluoroscopic systems, isocentric C-arm fluoroscopic systems, 3D fluoroscopic systems, O-Arm® imaging system, etc.

An optional imaging device controller 34 can control the imaging device 28 to capture the x-ray images received at the receiving section 32 and store the images for later use. The controller 34 may also be separate from the C-arm 28 and/or control the rotation of the C-arm 28. For example, the C-arm 28 can move relative to the subject 26, such as rotate about a longitudinal axis 26a of the patient 26, allowing anterior or lateral views of the patient 26 to be imaged. Each of these movements involves rotation about a mechanical axis 36 of the C-arm 28.

The operation of the C-arm 28 is understood by one skilled in the art. Briefly, x-rays can be emitted from the x-ray section 30 and received at the receiving section 32. The receiving section 32 can include a camera that can create the image data from the received x-rays. It will be understood that image data can be created or captured with any appropriate imaging device, such as a magnetic resonance imaging system, a positron emission tomography system, or any appropriate system. It will be further understood that various imaging systems can be calibrated according to various known techniques. The imager tracking device 38' can be provided to track a position of the receiving section 32 of the imaging device 28 at any appropriate time by the navigation system 20.

The image data can then be forwarded from the C-arm controller 34 to a navigation computer and/or processor 40 via a communication system 41. The navigation processor 40 can include a processor that is configured to operate to navigate a procedure, including a general purpose processor or computer executing instructions for navigation. The communication system 41 can be wireless, wired, a hardware data transfer device (e.g. a physical-ROM and/or rewritable flash memory), or any appropriate system. A work station 42 can include the navigation processor 40, the display 22, a user interface 44, and an accessible memory system 46. It will also be understood that the image data need not necessarily first retained in the controller 34, but may be directly transmitted to the workstation 42 or to a tracking system 50, as discussed herein. The workstation 42 can be any appropriate system such as a substantially portable computer and/or processor system with an integrated display 22. The workstation 42 may include a substantially portable computer, such as known laptop or tablet computer configurations, further including ruggedized laptop computer configurations.

The work station 42 provides facilities for displaying the image data as an image on the displays 22, saving, digitally manipulating, or printing a hard copy image of the of the received image data. The user interface 44, which may be a keyboard, mouse, touch pen, touch screen, or other suitable device, allows the user 21 to provide inputs to control the imaging device 28, via the C-arm controller 34, or adjust the display settings of the display 22. The work station 42 can also be used to control and receive data from a coil array controller (CAC)/navigation probe or device interface (NDI) as discussed herein.

While the optional imaging device 28 is shown in FIG. 1, any other alternative 2D or 3D imaging modality may also be used. For example, any 2D 3D imaging device, including one that can collect images in time, such as isocentric fluoroscopy, bi-plane fluoroscopy, ultrasound, computed tomography (CT), multi-slice computed tomography (MSCT), O-Arm® imaging device (sold by Medtronic, Inc.), T1 weighted magnetic resonance imaging (MRI), T2 weighted MRI, high frequency ultrasound (HIFU), positron emission tomography (PET), optical coherence tomography (OCT), intra-vascular ultrasound (IVUS), ultrasound, intra-operative CT, single photo emission computed tomography (SPECT), or planar gamma scintigraphy (PGS) may also be used to acquire 2D or 3D pre- or post-operative and/or real-time images or image data of the patient 26. The images may also be obtained and displayed in two or three dimensions and in time. In more advanced forms, surface rendering regions of the body may also be achieved by incorporating patient data or other data from an atlas or anatomical model map or from pre-operative image data captured by MRI, CT, or echocardiography modalities and displaying it in time. A more detailed discussion on optical coherence tomography (OCT), is set forth in U.S. Pat. No. 5,740,808, issued Apr. 21, 1998, entitled "Systems And Methods For Guiding Diagnostic Or Therapeutic Devices In Interior Tissue Regions" which is hereby incorporated by reference.

Image datasets from hybrid modalities, such as positron emission tomography (PET) combined with CT, or single photon emission computer tomography (SPECT) combined with CT, can also provide functional image data superimposed onto anatomical data to be used to confidently reach target sites within the patient 26. It should further be noted that the optional imaging device 28, as shown in FIG. 1, may be used to provide a virtual bi-plane image using a single-head C-arm fluoroscope as the optional imaging device 28 by simply rotating the C-arm 28 about at least two planes, which may be orthogonal planes to generate two-dimensional images that can be converted to three-dimensional volumetric images. By acquiring images in more than one plane, an icon representing the location of an impacter, stylet, reamer driver, taps, drill, deep brain stimulators, electrical leads, needles, implants, probes, or other instrument, introduced and advanced in the patient 26, may be superimposed in more than one view on the display 22 allowing simulated bi-plane or even multi-plane views, including two and three-dimensional views.

With continuing reference to FIG. 1, the navigation system 20 can further include the tracking system 50 that includes one or more localizers, such as an electromagnetic (EM) localizer 52, (e.g. which can also be referred to as a transmitter array, a tracking array, tracking coils, or coil array and can include a transmitter and/or receiver coil array) and/or an optical localizer 53. The tracking system 50 is understood to not be limited to any specific tracking system modality, e.g. EM, optical, acoustic, etc. Any appropriate tracking system modality can be used according to the present disclosure. Moreover, any tracked instrument, such as the instrument 24 and/or the dynamic reference frame (DRF) 58 can include one or more tracking devices that operate with one or more tracking modalities. Thus, the tracking system 50 can be selected to be any appropriate tracking system, including the StealthStattion® S7® surgical navigation system that offers both optical and AxiEM™ electromagnetic tracking options.

One skilled in the art will understand that the coil array 52 can transmit or receive and reference to the coil array 52 as a transmitter or a transmit coil array is merely exemplary and not limiting herein. The tracking system 50 can further include a coil array controller (CAC) 54 that can have at least one navigation interface or navigation device interface (NDI) 56 for connection of the localizer 52, an instrument tracking device 57 on or associated with the instrument 24, and a dynamic reference frame 58. The coil array controller 54 and the at least one navigation interface 56 can be provided in a single substantially small CAC/NDI container 60.

In the optical system, generally the localizer 53 includes one or more cameras that "view" the subject space. Tracking devices include members that are viewable by the cameras. The optical tracking devices may include one or more passive or active portions. An active tracking device can emit a viewable wavelength, including infrared wavelengths. Passive tracking devices can reflect selected wavelengths, including infrared wavelengths.

With continuing reference to FIG. 1 and initial reference to FIGS. 2A-6 the dynamic reference frame 58 according to various embodiments is illustrated and discussed. The dynamic reference frame 58 can be provided in various embodiments, including, for example, the dynamic reference frame 200, 300, and 400. Each dynamic reference frame generally includes a tracking device associated with a reference arm or member and a fixation portion. The fixation portion can be connected to the subject 26 at a selected position. Generally, the reference arm can move relative to the fixation portion. The dynamic reference frame 58 can include the tracking device 58a that is formed integrally with the dynamic reference frame member or as a separate portion affixed to the reference arm. For example, the tracking device can be connected directly to the patient 26, including a skull of the patient 26 or a head-holder, such as the MAYFIELD® Composite Series Skull Clamp including those sold by Integra LifeSciences Corporation having a place of business at Plainsboro, N.J., USA.

One skilled in the art will understand that the tracking device 58a according to various embodiments, can be any appropriate device and can be an emitter, a receiver, a reflector, a sensor to sense a field, or any other appropriate device that can be tracked by a tracking system including a localizer. Also the tracking device can be wired to the other portions of the system 20 or have a wireless communication therewith, as discussed herein.

The tracking system can include the EM localizer 52, the EM localizer 52 can include that described in U.S. patent application Ser. No. 10/941,782, filed Sep. 15, 2004, now U.S. Pat. No. 7,751,865, issued Jul. 6, 2010, and entitled "METHOD AND APPARATUS FOR SURGICAL NAVIGATION", herein incorporated by reference. The localizer may also be supplemented and/or replaced with a second localizer or other localizer. As is understood the localizer 52, according to any of the various embodiments, can transmit signals that are received by the dynamic reference frame 58, and a tracking device that is associated with (e.g. connected to) the instrument 24. The dynamic reference frame 58 and the tracking device can then transmit signals based upon the received/sensed signals of the generated fields from one or more of the localizers 52. Moreover, the tracking system 50 may include or operate with the optical localizer 53. Optical tracking systems can include the StealthStation® S7® Surgical Navigation System, sold by Medtronic Navigation, Inc. The optical localizer can view the subject space and the tracking devices associated with the DRF 58 and/or the instrument 24. Generally, the optical localizer 53 includes at least two cameras that allow for a determination of distance.

It should further be noted that the entire tracking system 50 or parts of the tracking system 50 may be incorporated into other portions in the operating theatre. Incorporating and/or integrating the tracking system 50, or at least portions thereof, may provide an integrated system. The integrated system can provide for various features such as known or reduced field interference or distortion.

For example, one of the localizers, or any appropriate or selected portion of the tracking system 50, can be incorporated into the imaging device 28. The transmitter coil array 52 can be attached to the receiving section 32 of the C-arm 28. It should be noted, however, that the transmitter coil array 52 may also be positioned at any other location as well. For example, the transmitter coil array 52 may be positioned at the x-ray source 30.

The localizer 52, according to various embodiments, can include a coil array that is used in an electromagnetic tracking system. The localizer 52 may also be positioned in the items being navigated, further discussed herein, including the instrument 24. Also, the coil array of the localizer 52 can include a plurality of coils that are each operable to generate distinct electromagnetic fields into the navigation region of the patient 26, which is sometimes referred to as patient space. Electromagnetic systems are generally described in U.S. Pat. No. 5,913,820, entitled "Position Location System," issued Jun. 22, 1999 and U.S. Pat. No. 5,592,939, entitled "Method and System for Navigating a Catheter Probe," issued Jan. 14, 1997, each of which are hereby incorporated by reference.

Coil arrays 52a of the localizer 52 are controlled or driven by the coil array controller (CAC) 54. The CAC 54 can transmit a signal with a transmission line 521 to the respective localizer 52. The coil array of the localizer 52 can have more than one coil that is driven by the coil array controller 54 in a time division multiplex, a frequency division multiplex manner, or selected appropriate manner. Each coil array can include an array of coils provided to generate a selected field. For example, at least three substantially orthogonal coils may generate three substantially orthogonal fields. In this regard, each coil of the coil array 52a may be driven separately at a distinct time or all of the coils may be driven simultaneously with each being driven by a different frequency, as discussed further herein. It is understood, however, that any selected number of coils can generate a diverse field that can be resolved for tracking a tracking device. Also, individual coils can be driven at more than one frequency simultaneously.

Upon driving the coils in the coil array 52a with the coil array controller 54, electromagnetic fields are generated within the patient 26 in the area where the medical procedure is being performed, which is again sometimes referred to as patient space. The electromagnetic fields generated in the patient space induce currents in the tracking devices positioned on or in the instruments 24. These induced signals from the instrument 24 are delivered to the navigation device interface 56 and can be forwarded to the coil array controller 54. The navigation probe interface 56 may provide all the necessary electrical isolation for the navigation system 20, as discussed herein. The navigation device interface (NDI) 56 can also include amplifiers, filters and buffers to directly interface with the tracking devices. Alternatively, the tracking devices or any other appropriate portion, may employ a wireless communications channel, such as that disclosed in U.S. Pat. No. 6,474,341, entitled "Surgical Communication Power System," issued Nov. 5, 2002, herein incorporated by reference, as opposed to being coupled with a physical transmission line to the NDI 56.

When the navigation system 20 uses an EM based tracking system, various portions of the navigation system 20, such as tracking devices are equipped with at least one, and generally more coils that are operable with the EM localizer 52. Alternatively, the tracking system may be a different or a hybrid system that includes components from various tracking systems such as optical, acoustic, etc.

The EM tracking device 57 on the instrument 24 can be in a handle or inserter that interconnects with an attachment and may assist in placing an implant or in driving a portion. The instrument 24 can include a graspable or manipulable portion at a proximal end and the tracking sensor device that can be fixed near the manipulable portion of the instrument 24 or at a distal working end, as discussed herein. The tracking device 57 can include an electromagnetic sensor to sense the electromagnetic field generated by the localizer 52 that can induce a current in the tracking device 57, if the tracking device 57 is a conductive coil for an EM tracking device.

The dynamic reference frame (DRF) 58 of the tracking system 50 can also be coupled to the NDI 56 to forward the information to the CAC 54 and/or directly to the processor 40. The DRF 58, according to various embodiments, may include a tracking device 58a, the tracking device 58a may include a magnetic and/or electromagnetic field detector, optical emitter or reflector, acoustic emitter or sensor, etc. If the dynamic reference frame 58 is electromagnetic it can be configured as a pair or trio of substantially mutually orthogonally oriented coils, each having the same center or may be configured in any other non-coaxial or co-axial coil configurations.

The DRF 58 may be fixed to the patient 26 adjacent to the region where navigation is occurring so that any movement of the patient 26 is detected as relative motion between the localizer 52 and the dynamic reference frame 58. The dynamic reference frame 58 can be interconnected with the patient 26 in any appropriate manner, including those discussed herein. Any relative motion is forwarded to the coil array controller 54, which updates registration correlation and maintains accurate navigation, further discussed herein. The tracking device 58a of the DRF 58 may be positioned in at least two known positions, as discussed herein. For example, the tracking device 58a can be placed in a first position 58a' and a second position 58a".

The dynamic reference frame 58 may be affixed externally to the patient 26, adjacent to the region of navigation, such as on the patient's skull, chest, spine, etc. The dynamic reference frame 58 can be affixed to the patient's skin, by way of a selected adhesive patch and/or a tensioning system. The dynamic reference frame 58 may also be removably attachable to a fiducial marker. The fiducial markers can be anatomical landmarks or members attached or positioned on the patient's 26 body. The dynamic reference frame 58 can be connected to a bone portion of the anatomy, such as the skull. The bone portion can be adjacent, the area of the procedure, the bone of the procedure, or any appropriate bone portion.

Briefly, the navigation system 20 operates as follows. The navigation system 20 creates a map between all points in the image data or image space and the corresponding points in the patient's anatomy in subject or patient space. After this map is established, the image space and subject space are registered. In other words, registration is the process of determining how to correlate a position (i.e. a location and orientation) in image space with a corresponding point in real or subject space. This can also be used to illustrate a position of the instrument 24 relative to the proposed trajectory and/or the determined anatomical target. The work station 42 either alone or in combination with the coil array controller 54 and/or the C-arm controller 34 identify the corresponding point on the acquired image (which can be pre-acquired image data) or atlas model relative to the tracked instrument 24 and display the position on display 22 and relative to an image 25 that is based on or generated with acquired or accessed image data. Each of the systems described above may also be incorporated into a single system or executed by a single processor. This identification is known as navigation or localization. An icon representing the localized point or instruments is shown on the display 22 within several two-dimensional image planes, as well as on three dimensional images and models and any of these shown in time. Also, the shown points, instruments, and/or icons can be based on models of the various items and points.

To register the patient 26 to the image 25, the user 21 may use point registration. Generally the DRF 58 is first attached to the subject 26. Point registration then proceeds by selecting and storing particular points from the pre-acquired images and then touching the corresponding points on the patient's anatomy with a pointer probe or any appropriate tracked device, such as the instrument 24. The navigation system 20 analyzes the relationship between the two sets of points that are selected and computes a match, which allows for a determination of a correlation of every point in the image data or image space with its corresponding point on the patient's anatomy or the patient space.

The points that are selected to perform registration or form a map are the fiducial markers, such as anatomical or artificial landmarks. Again, the fiducial markers are identifiable on the image 25 and identifiable and accessible on the patient 26. Fiducial markers can be artificial landmarks that are positioned on the patient 26 or anatomical landmarks that can be easily identified in the image data. The artificial fiducial markers can also form part of the dynamic reference frame 58, such as those disclosed in U.S. Pat. No. 6,381,485, entitled "Registration of Human Anatomy Integrated for Electromagnetic Localization," issued Apr. 30, 2002, herein incorporated by reference. It will be understood that any appropriate number of the fiducial markers can be provided with and/or separate from the DRF 58.

The navigation system 20 may also perform registration using anatomic surface information or path information as is known in the art (and may be referred to as auto-registration). The navigation system 20 may also perform 2D to 3D registration by utilizing the acquired 2D images to register 3D volume images by use of contour algorithms, point algorithms or density comparison algorithms, as is known in the art. An exemplary 2D to 3D registration procedure is set forth in U.S. Ser. No. 10/644,680, filed on Aug. 20, 2003, now U.S. Pat. No. 7,570,791, issued Aug. 4, 2009, entitled "Method and Apparatus for Performing 2D to 3D Registration", hereby incorporated by reference.

In order to maintain registration accuracy, the navigation system 20 continuously can track the position of the patient 26 during registration and navigation with the dynamic reference frame 58. This is because the patient 26, dynamic reference frame 58, and localizer 52 may all move during the procedure, even when this movement is not desired. Alternatively the patient 26 may be held immobile once the registration has occurred, such as with a head holder. Therefore, if the navigation system 20 did not track the position of the patient 26 or area of the anatomy, any patient movement after image acquisition would result in inaccurate navigation within that image. The dynamic reference frame 58 allows the tracking system 50 to track the anatomy and can assist in registration. Because the dynamic reference frame 58 is rigidly fixed to the patient 26 at least with a fixation portion, as discussed herein, any movement of the anatomy or the localizer 52, 53 is detected as the relative motion between the localizer 52, 53 and the dynamic reference frame 58. This relative motion is communicated to the workstation 42, such as via the coil array controller 54, via the navigation probe interface 56, which updates the registration correlation to thereby maintain accurate navigation. The optical localizer 53 may also communication via the controller 54 and/or directly with the workstation 42 to communicate the tracked portion of the various tracking devices.

The dynamic reference frame 58 can be affixed to any appropriate portion of the patient 26, and can be used to register the patient to the image data, as discussed above. For example, when a procedure is being performed relative to the skull or spine. The dynamic reference frame 58 can be interconnected with the subject in any appropriate manner, such as those discussed herein according to various embodiments.

Navigation can be assisted with registration and the navigation system 20 can detect both the position of the patient's anatomy and the position of the tracking device attached to the instrument 24. Knowing the location of these two items allows the navigation system 20 to compute and display the position of the instrument 24 or any portion thereof in relation to the patient 26. The tracking system 50 is employed to track the instrument 24 and the patient 26 simultaneously.

The tracking system 50, if it is using an electromagnetic tracking assembly, can work by positioning the EM localizer 52 near the subject space to generate an electromagnetic (EM) field, which can be low energy and also generally referred to as a navigation field. Because every point in the navigation field or patient space is associated with a unique field strengths and directions, the electromagnetic tracking system 50 can determine the position of the instrument 24 by measuring the field strengths, directions, and/or components thereof at the tracking device location. If the tracking system is using the optical localizer 53 the one or more cameras view the subject and define the subject space which can also be referred to as the navigation space. The optical tracking system can use one or more cameras to define the navigation space. For example, a view of the tracking devices can be used to determine a distance, such as by triangulation from the optical localizer 53 to determine a location of the tracking device.

The dynamic reference frame 58 is fixed to the patient 26 to identify the position of the patient 26 in the navigation field. The tracking system 50 continuously recomputes the relative position (including location and orientation) of the dynamic reference frame 58 and the instrument 24 during localization and relates this spatial information to patient registration data to enable image guidance of the instrument 24 within and/or relative to the patient 26.

To obtain a maximum accuracy it can be selected to fix the dynamic reference frame 58 in each of at least six-degrees of freedom. Thus, the dynamic reference frame 58 or any tracking device can be fixed relative to axial motion X, translational motion Y, rotational motion Z, yaw, pitch, and roll relative to the portion of the patient 26 to which it is attached. Any appropriate coordinate system can be used to describe the various degrees of freedom. Fixing the dynamic reference frame relative to the patient 26 in this manner can assist in maintaining maximum accuracy of the navigation system 20.

The instrument 24 can be any appropriate instrument (e.g., a catheter, a probe, a guide, etc.) and can be used for various mechanisms and methods, such as delivering a material to a selected portion of the patient 26, such as within the cranium or spine. The material can be any appropriate material such as a bioactive material, a pharmacological material, a contrast agent, or any appropriate material. As discussed further herein, the instrument 24 can be precisely positioned via the navigation system 20 and otherwise used to achieve a protocol for positioning the material relative to the patient 26 in any appropriate manner. The instrument 24 may also include a brain probe to perform deep brain stimulation. The instrument including the tracking device 57 can also be used to track the user 21.

As discussed above, registration can occur between image data of the patient that can be displayed as the image on the display device and the navigation space defined by the localizer. As an example, with reference to FIGS. 2A and 2B, the tracking system can track a dynamic reference frame 200 that is associated with the patient 26, the DRF 200 can be the DRF 58 discussed in general above. The dynamic reference frame 200 can be interconnected with the patient to any appropriate manner or at a location appropriate for a selected procedure. For example, during a spinal procedure, the DRF 200 can be connected with a selected vertebra (shown in phantom in FIG. 2A) of the patient with a fixation or mounting portion, such as with a clamp or arm portion 202. The clamp portion 202 can include a first leg 204 and a second leg 206 that can include one or more projections 208 to compress or engage a vertebrae portion, such as a spinal process of a vertebrae, as illustrated in phantom. A mechanism, such as a screw or clamping member 212 can be used to move one or both of the legs 204 and 206 towards one another to securely engage the vertebrae. Further details of the DRF 200 are discussed below and included in U.S. Pat. No. RE42,226, issued on Mar. 15, 2011, entitled PERCUTANEOUS REGISTRATION APPARATUS AND METHOD FOR USE IN COMPUTER-ASSISTED SURGICAL NAVIGATION, incorporated herein by reference.

The DRF 200 can further include a second portion, such as a reference arc or reference arm assembly 220. The reference arm assembly 220 is moveable and fixable relative to the clamping portion 202. The reference arm assembly 220 can include a reference arm 222 that engages the clamping portion 202 through an adjustment assembly or mechanism 230. The adjustment assembly 230 can include an adjustable screw or locking member, such as a set screw 232.

The arm 222 can move a tracking device holding arm 240 relative to the clamp portion 202. For example, the arm can move along an axis generally in the direction of arrows 242 to change a distance of the reference arm 240 from the clamp member 202. Additionally, the arm can move with the adjusting assembly 230 angularly relative to the clamping member 202, such as generally along an arc or a curve as illustrated by arrow 244. The set screw 232 can be operated to engage and disengage a first arm portion 222*a* and a second arm portion 222*b* of the arm 222, as further illustrated in FIG. 2B. Thus, the arm 222 can move from a first position and/or orientation 240*a* relative to the mounting portion 202, as illustrated in solid lines in FIG. 2A, to a second position and or orientation 240*b*, as illustrated in phantom lines in FIG. 2A, to alter the position and/or orientation of the reference arm 240 from the first position 240*a* to the second position at 240*b* relative to the clamp portion 202.

The reference arm 240 can include one or more tracking devices. For example, four tracking devices 250A-250D can be connected to the reference arm 240. The tracking devices 250A-250D can be appropriate tracking devices. For example, the tracking devices 250A-250D can each include light emitters or reflectors for an optical tracking system. Alternatively, or in addition thereto, there may be only one of the tracking devices 250A-D that can include one or more coils of a conductive material that can be used to sense an electromagnetic field. It is also understood, that each of the tracking devices 250A-250D can include one or more coils of conductive material. As discussed above, the tracking system 50 can generate an electro-magnetic field that can be sensed by the tracking devices 250A-250D to determine a position of the tracking devices. The tracking devices 250*a*-*d* may also be other appropriate tracking devices, such as light emitters and/or reflectors for use with the optical localizer 53.

Figure 2A:
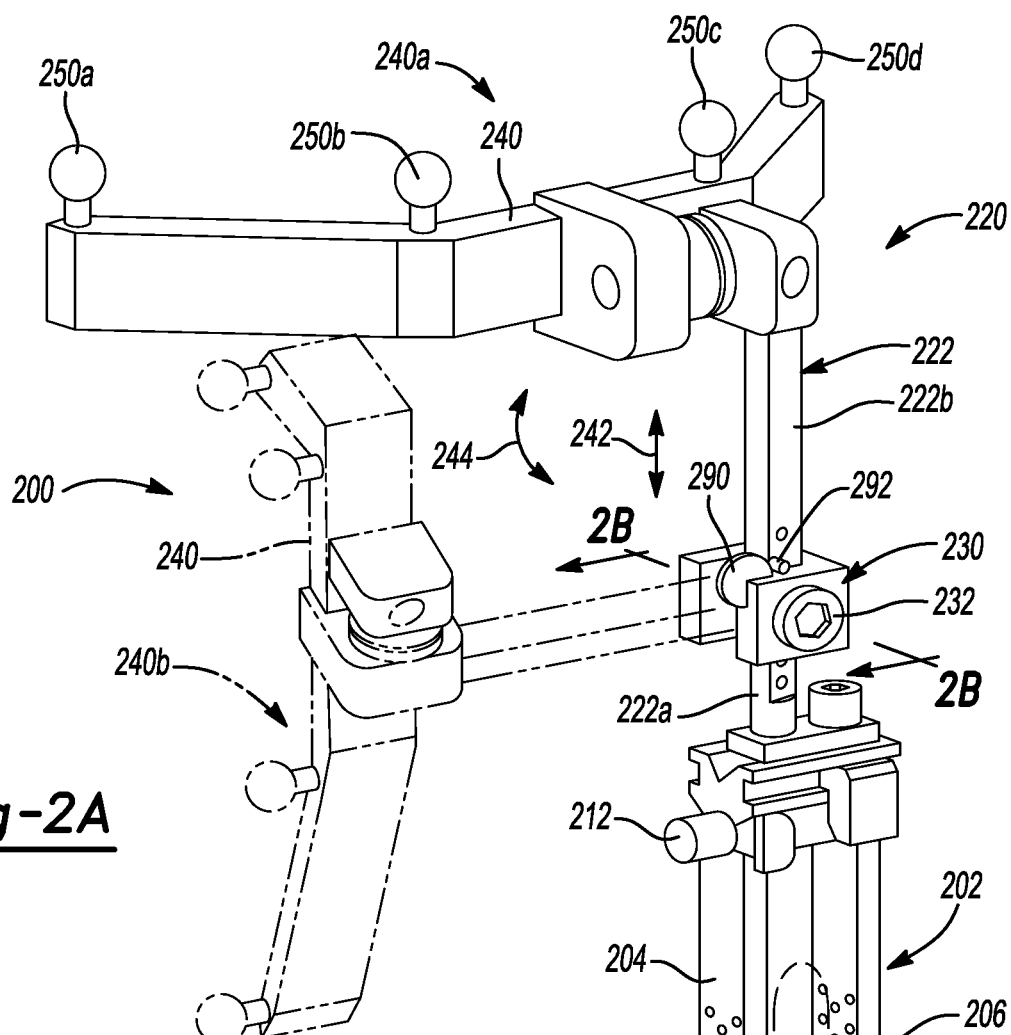
FIG. 2A is a plan view of a dynamic reference frame, according to various embodiments.

When the reference arm 240 moves from the first position 240*a* to the second position 240*b*, the tracking devices 250A-250D, which are fixed to the reference arm 240, move relative to the clamp member 202. As illustrated in FIG. 2A, the geometry of the DRF 200 can be changed between at least two known positions. It is understood, however, that the geometry of the tracking devices 250A-250D relative to the clamp member 202 can be altered to any appropriate number of positions. As illustrated in FIG. 2A, the first position 240*a* and the second position 240*b* can be different configurations of the reference arm 240 relative to the mounting portion 202 in Cartesian coordinates, including X, Y, and Z axes and orientation. Thus, the DRF 200 can include a mounting portion 202 that is fixable in one position and orientation, such as by clamping, relative to a subject and a second portion including the reference assembly that is moveable relative to the mounting portion 202. The movement of the reference assembly 240 allows the mounting portion to remain fixed, but move another portion that is obstructing a users vision, work space etc.

Figure 2B:
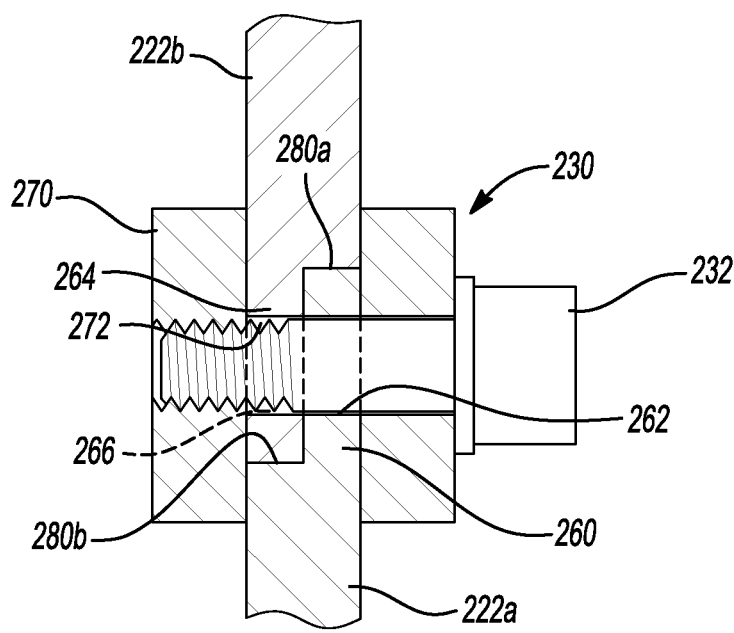
FIG. 2B is a detail view of a portion of the dynamic reference frame of FIG. 2A illustrating an adjustment portion.

With reference to FIG. 2B, and continuing reference to FIG. 2A, the moving or adjustment assembly 230 is illustrated in further detail. As discussed above, the moving assembly 230 can include a set screw 232. The adjustment assembly allows the reference arm 240 to move relative to the mounting portion 202 without requiring movement of the mounting portion 202.

The first arm portion 222A, the second arm portion 222B can each include a mating portion. The mating portion of the first arm portion 222A can include a finger 260 that includes a throughbore 262 and at least one surface 280*a*. The second arm portion 222B can include a second finger 264 and a second throughbore 266 and at least one surface 280*b*. The adjustment assembly 230 can further include an external member or housing 270 that further includes a threaded bore or blind bore 272. The set screw 232 can engage the blind bore 272 in the housing 270 and provide a clamping or fixation force for the adjustment assembly 230. The adjustment assembly 230, therefore, can allow for movement of the second arm 222B relative to the first arm portion 222A.

The mating portions can allow for a repeatable selected positioning of the second arm portion 222B relative to the first arm portion 222A by engaging the surfaces of the mating portions. For example, the second arm portion 222B can include the shoulder or engaging surface 280*b* that is substantially flat or has a selected contour that will engage only an end or surface 280a of the finger 260 or a side of the finger 260. Thus, the second arm portion 222B is will substantially only fixedly mate securely, for navigation, at selected positions. Thus, the DRF 200 can offer movement of the reference arm 240 between selected and known geometries, including different positions and orientations relative to the clamp member 202.

The repeatable and secure positions of the reference arm 240 relative to the clamping member 202 can be known. For example, the repeateable positions can be limited and saved in the accessible memory of the system 42. For example, a marking on the adjustment assembly 230 can be viewed and a value (e.g. a measurement or selected number) can be input into the processor system to recall the known geometry and configuration of the reference arm 240 relative to the mounting portion 202. Also, as discussed herein, the position of the reference arm can be determined with a tracking or reference probe that is tracked with the tracking system 50 and touches the reference arm 240. Also, a sensor assembly can be positioned between the mounting portion 202 and the reference arm 240. For example, a first sensor portion 290 may be placed on the adjustment assembly 230 and a second sensor portion 292 can be placed on the arm portion 222b. The relative positions of the two sensor portions 290, 292 can be used to send a signal to the processor system 40 to recall a known configuration of the DRF 200 based on the input. The sensor can include an appropriate sensor assembly, including an encoder, a magnetic sensor, a switch, etc. Also, a tracked location of the tracking devices 250 can be used to determine a moved location of the reference arm 240. For example, a large or drastic movement (e.g. greater than about 4 cm) of the reference arm 240 over a short period of time (e.g. less than about three seconds) can be used to signal that a change in position and/or orientation of the reference arm 240 has been made. The tracking system can then track the new position and/or orientation and a signal can be sent to the processor system 40 to recall the current position and/or orientation. Nevertheless, movement of the reference arm 240 is made relative to the clamp portion 202 that is fixed to the subject 26.

With reference to FIG. 3, a DRF 300 is illustrated. The DRF 300 can be used as the DRF 58 and can be fixed to the subject 26, the DRF 300 can include different portions for connection and movement relative to the patient 26. The DRF 300 can include a threaded member or screw 310 that includes a threaded core or shaft 312 and a head 314. The head 314 can be engaged to twist or drive the threaded body 312 into the patient 26, such as a vertebrae of the patient. Further, a shaft or extension member 320 can extend from the head 314. The shaft 320 can be formed as a single member or configured to couple with the head 314 such that a cannula 324 that passes through the extended arm 320 can align with a head bore 326. The cannula 324 and the head bore 326 can allow for passage of a guide wire or fixation wire to rotatably fix the extension member 320 and the head 314 relative to a selected portion of the subject, as described in U.S. Pat. No. RE42,226, issued on Mar. 15, 2011, entitled PERCUTANEOUS REGISTRATION APPARATUS AND METHOD FOR USE IN COMPUTER-ASSISTED SURGICAL NAVIGATION, incorporated herein by reference.

Coupled to the extension arm or shaft 320 can be a reference assembly or portion 340. The reference assembly 340 can include a central hub 342 that has a central bore or passage 344 that mates and/or contacts with an outer surface 346 of the extension arm 320. The bore 344 can be keyed relative to the outer surface 346 such that the reference assembly 340 does not rotate relative to the external surface 346 once positioned to mate with the external surface 346. Additionally, the reference assembly 340 can be selectively or moveably positioned relative to the extension shaft 320 in a selected plurality of positions. For example, the external surface 346 can be non-circular, such as hexagonal, octagonal, or etc. in cross-section. The bore 344 can include a complimentary internal surface cross-section such that it will non-rotationally mate with the external surface 346. However, if the external surface 346 has a hexagonal external cross-section and the bore 344 includes an internal hexagonal cross-section, the reference assembly 340 can be positioned at least at six discrete positions around the extension member 320. The reference assembly 340 can be rotated in the direction of arrow 350 around a central axis 352 of the extension member 320 to achieve one of the selected discrete positions. A set screw or locking screw or other locking member 360 can engage the extension shaft 320, either internally in the cannula 324, or externally on the surface 346 to engage the central hub 342 of the reference assembly 340. A shelf or shoulder 362 can counter engage the hub 342 to lock the reference assembly 340 in the selected position around the central shaft.

With continuing reference to FIG. 3 and additional reference to FIG. 4, the reference assembly at 340 can include a plurality of spokes or arms 370A-370D. Associated or connected to the each of the arms or spokes 370A-370D can be one or more tracking devices 380A-380D. Although any selected number of tracking devices can be used, including less or more than four. As discussed above, the tracking devices 380A-380D can be any appropriate tracking devices such as optical tracking devices, EM tracking devices, ultrasonic tracking devices, or similar tracking devices. As illustrated in FIG. 4, the reference assembly 340 can be rotated generally in the direction of arrow 350.

The reference array 340 can be positioned in a first geometry or configuration 340a shown in solid lines. The reference array can then, for example, be moved to a second geometry or configuration 340b shown in dashed lines. The reference array 340 can be rotated, such as about 45° as illustrated in FIG. 4, to alter a configuration of the reference array 340 relative to the screw body 312. As discussed above, the screw body 312 can be fixed at a single orientation relative to the patient 26 by threading the screw body 312 into the patient and further fixing a guide wire through the cannula 324 and the head passage 326. Thus, rotating the reference array 340 relative to the screw body 312 will change an orientation and/or position of the reference assembly 340 relative to the patient 26. Additionally, as discussed above, the extension body 320 can have a selected configuration such that the reference assembly 340 can be moved to selected discrete orientations relative to the screw assembly 310.

Accordingly, the reference assembly 340 can be moved to one or more known configurations including a position and/or orientation relative to the patient 26 at a selected time, such as prior to or during a procedure, as further discussed herein. Again, each of the configurations can be previously known or determined and save and/or determined during a procedure. The different configuration can be based on the mounting portion of the DRF 300, including the screw 312, remaining at a single fixed position and orientation relative to the subject when the reference array 340 is in any of the known configurations. An input to the processor 40 regarding the configuration of the reference array 340 of the DRF 300 can be made according to any appropriate input, as discussed above. The configuration of the DRF 300 can be determined according to the mechanisms and systems, including those discussed above, such as a sensor, inputting a position, etc.

Figure 5:
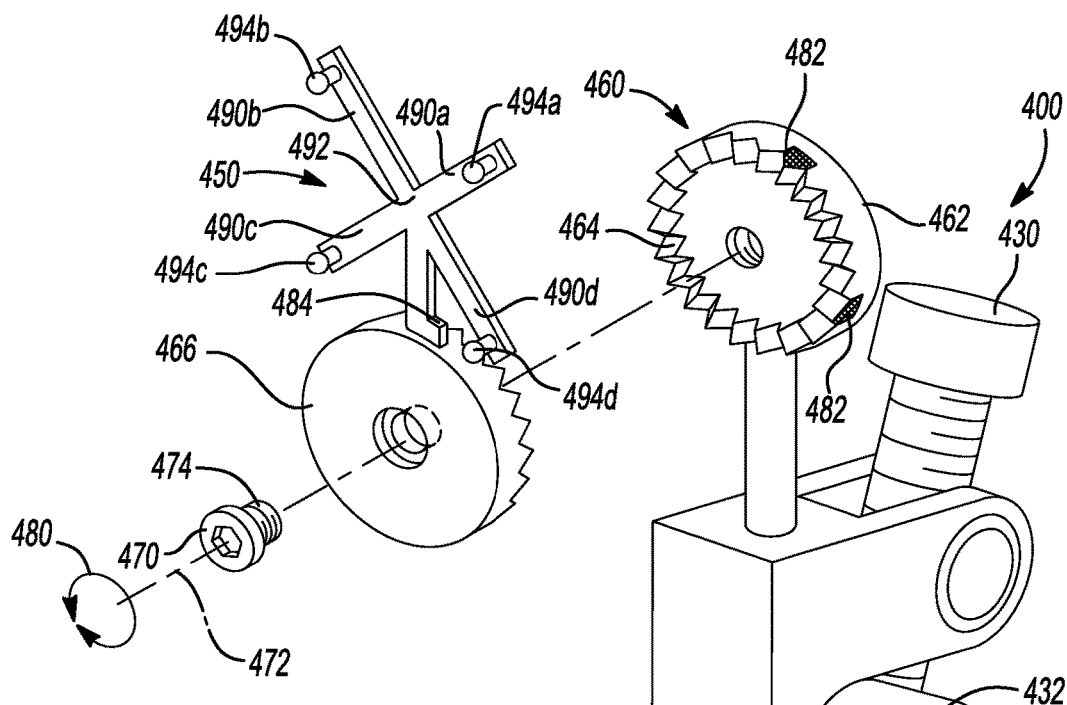
FIG. 5 is a plan view of a dynamic reference frame, according to various embodiments.

With reference to FIG. 5, a dynamic reference frame 400 is illustrated. The DRF 400 can be used as the DRF 58 discussed above. The DRF 400 can include a mounting portion or subject engagement assembly 420 similar to that disclosed in U.S. Pat. No. 8,350,730, issued on Jan. 29, 2013, and incorporated herein by reference. Generally, the clamping member 420 includes members, such as a first leg member 422 and second leg member 424, to engage a portion of the patient 26 such as a spinous process of a vertebra. Projections or spike members 426 can extend from one or both of the legs 422 and 424 to further engage the patient 26. The clamping member 420 can further include a manipulation or adjustment assembly, such as a screw 430. The screw 430 can engage the first leg member 424 and the second leg member 422. By turning the screw 430, the first leg member 422 can pivot about a pivot point 432 to move closer or further away from the second leg member 424. Thus, the clamping assembly 420 can be clamped onto a portion of the patient 26 in a selected location. The configuration of the clamping member 420 can ensure that the clamping member 420 remains substantially immobile relative to the patient 26 once positioned on the patient 26.

The DRF 400 can further include a reference array or arm 450 that can be interconnected with the clamping member 420 by an adjustment assembly, including a starburst connection assembly 460. The starburst connection assembly 460 can include a first starburst member 462 that has a ridged or ribbed face 464. The starburst assembly 460 can further include a second starburst member 466 that includes a second ribbed face (not specifically illustrated) to engage and/or contact the first ribbed face 464. The ribbed faces can include peaks and valleys extending generally radially from a center of each starburst member 462, 464. Each face can further can mate with one another such that one peak mates with a respective valley in the opposed face. A locking screw or member 470 can then engage the two starburst members 462 and 466 together to lock the two starburst members 462 and 466 in a selected location and orientation. The reference array 450 can, therefore, rotate about an axis 472 defined through the first starburst member 462 and also the second starburst member 466 when coupled to the first starburst member 462. The locking member 470 can have a threaded portion 474 that can engage a thread in the first starburst member 462 and/or a locking nut to lock the first and second starburst members 462 and 466 together in a selected orientation.

The reference array 450 can be rotated generally in the direction of arrow 480 around the axis 472 to orient the reference array 450 relative to the clamping member 420 in at least one selected geometry or configuration including a position and/or an orientation of a plurality of orientations and locations relative to the clamping member 420. In other words, the reference array 450 can be moved relative to the clamping member 420, while the clamping member remains in a single fixed location relative to the subject, as discussed above.

The geometry or configuration of the DRF 400, including the reference array 450 relative to the clamping member 420, can include a plurality of known configurations. The known configurations can be saved in the memory system 44, as discussed above, and recalled by the processor 40. The processor can recall the configuration based on selected inputs, such as a manual input from a user. For example, the first starburst member 462 can include markings or demarcations 482 to illustrate or identify a position of the reference array 450 relative to the first starburst member 462. For example, a pointer or indicator 484 can be positioned with the reference array to align with a selected one of the markings 482 of the first starburst array 462. The markings 482 can relate to a selected orientation or position of the reference array relative to the clamping member 420 for determining or selecting a position of the reference array 450 relative to the clamping member 420. The user can read the marking and input the markings for the processor 40 to recall the configuration. It is understood, however, that the input can include an automatic input from a sensor that senses the configuration of the DRF 400, tracking the reference array 450, or other selected inputs as discussed above.

The reference array 450 can be similar to the reference arrays discussed above. For example, the reference array can include one or more spokes or arms, such as four spokes 490A-490D that extend from a central hub or portion 492. One or more tracking devices can be associated with each of the spokes 490A-490D. For example, tracking devices 494A-494D can be positioned on the spokes or arms 490A-490D. The tracking devices can include optical tracking devices. Further, as discussed above the reference array 450 can include a single tracking device, such as a sensor coil.

Figure 6:
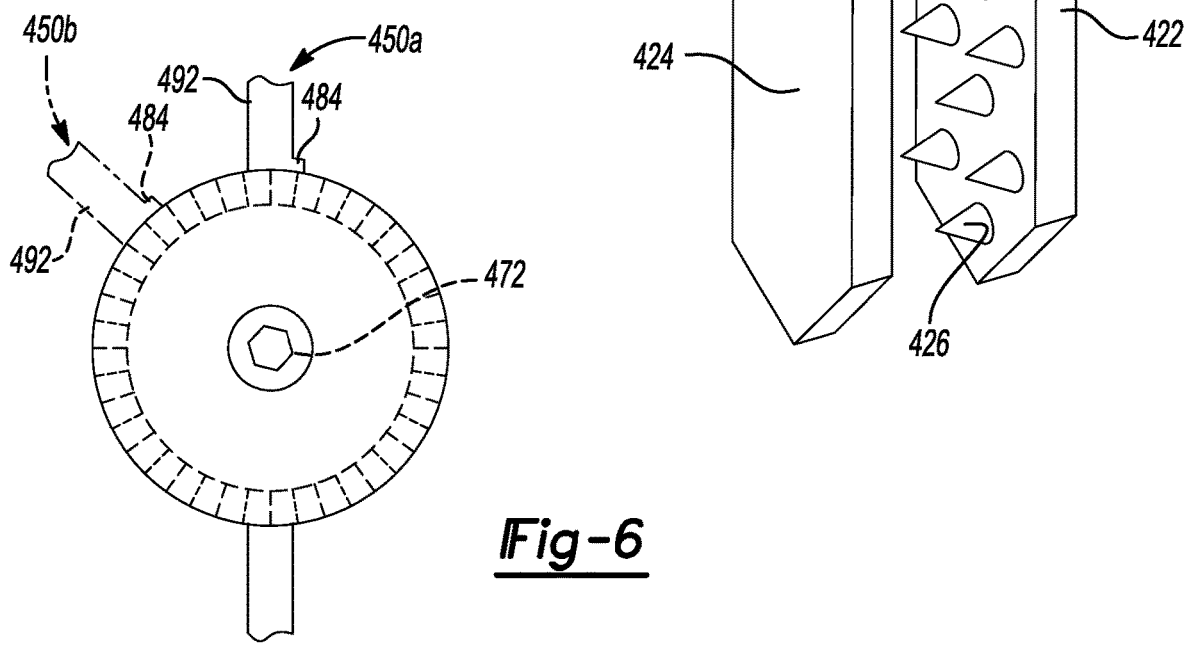
FIG. 6 is a schematic view of an alterable position of the dynamic reference frame of FIG. 5.

With continued reference to FIG. 5 and additional reference to FIG. 6, the reference array 450 can be rotated around the axis 472. As illustrated in FIG. 6 in solid lines the reference array 450 can be positioned at a first selected position 450a relative to the first starburst member 462. The indicator 484 can be read or positioned relative to the markings 482 in a selected position. With continuing reference to FIG. 6, a second orientation 450b of the reference array 450 can also be achieved or selected, as illustrated in phantom. The indicator 484 can also be used to indicate or read the position of the reference array 450 relative to the first starburst member 462 at the second location, illustrated in phantom. Also, as sensor, such as a voltage divider, potentiometer, counter, encoder, magnetic sensor, switch, etc. can be used to determine the rotated position of the array 450.

Thus, it is further understood, that the reference array 450 can be positioned at one or more of a plurality of selected known configurations, including an orientation and/or a position, relative to the clamping member 420 with at least the first starburst member 462. The first starburst member 462 can be disengaged from the second starburst member 466, then the reference array 450 can be pivoted around the axis 472, and the starburst members 462 and 466 can be reengaged. Again, each of the locations can be pre-determined or known. The user 21 can read the markings 482 and input the read marking value into the navigation system, the navigation system including the processor 40 can determine the current configuration, including position and/or location of the array 450 relative to the clamping member 420.

As discussed above, registration can be performed by various techniques. Once registration has occurred, the DRF 58, such as the DRFs described above according to various embodiments, can be used to track the location of the patient 26 in case of any movement to the patient 26 during a procedure after registration. Movement of the patient, as tracked by the dynamic reference frame, can be used to maintain registration of the patient space relative to the image space. The dynamic reference frame is fixed relative to a portion of the patient, such as a vertebra, a skull, or the like, to track a portion of the patient. Registration of the patient space can be made relative to the DRF. Accordingly, tracked movement of the DRF can be used to translate the movement of the patient space to the image space. However, the registration is maintained as long as the location and orientation of the reference arm of the DRF is known relative to the patient 26 after registration.

During a procedure, the user 21 may determine that the DRF that has been positioned relative to the patient 26 interferes with a portion of the procedure. For example, while performing a resection, implantation, or spinal fusion, it may be advantageous to move the reference arm of the DRF. As discussed above, the DRF can include a portion that allows movement of the reference arm from a first configuration, including a first position and/or orientation, to a second configuration, including a second position and/or orientation, as discussed above in relation to the figures. According to various embodiments, and as discussed in further detail herein, the registration can occur with a DRF in a first configuration, the DRF can later be moved to a second configuration, and the navigation system 10 can be used to maintain registration by applying an adjustment factor value to the initial registration based upon a changed or new configuration of the DRF, or at least the reference portion of the DRF. In other words, the registration initially performed is maintained although the configuration of the DRF has changed. As discussed above, a reference arm or array can be moved relative to a fixation portion, such as a clamp, that fixes the DRF to the patient 26. The adjustment factor can include a translation and/or orientation value (including a difference) for the reference arm relative to the subject fixation portion of the DRF.

Figure 7:
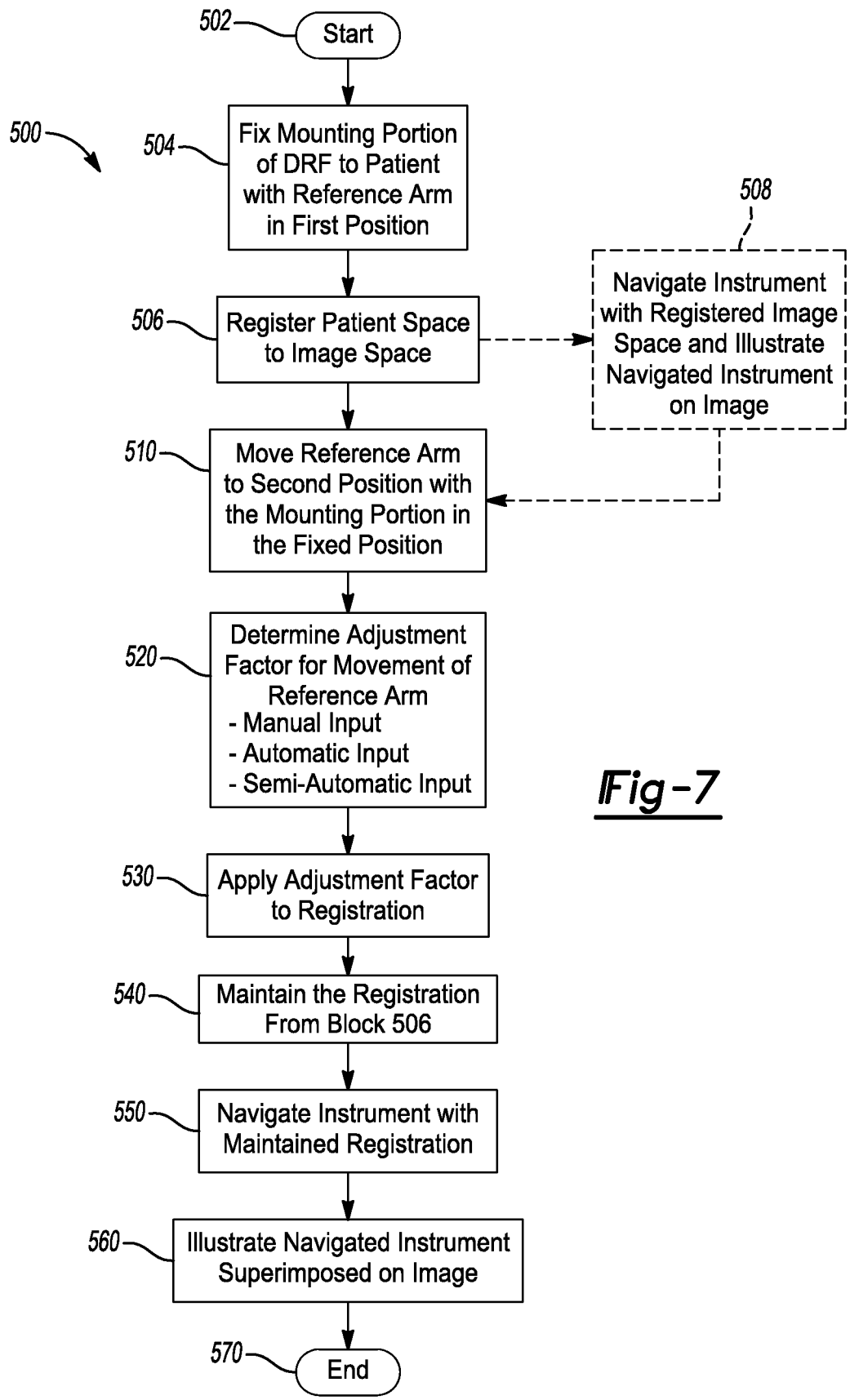
FIG. 7 is a flow chart of a method of maintaining a registration.

With reference to FIG. 7, a flowchart 500 for registering a patient space to an image space is illustrated. Initially, the procedure can begin in start block 502. The procedure can then proceed to block 504 where a DRF is fixed to the patient 26 with a reference arm in first position. For example, with reference to FIG. 5, the DRF can be fixed to the patient with the clamp portion 420 with the reference array 450 in the first orientation or position 450*a*, such as with the reference array 450 extending substantially parallel with the clamp portion 420. The patient space can be registered to the image space in block 506. Registration can proceed according to any appropriate registration procedure, including those discussed above. For example, the user 21 can touch or identify various portions on the patient 21 and touch or identify the same portions in the image 25 illustrated on the display 22. It is understood that the image 25 can be any appropriate image, and vertebrae merely exemplary.

Once the registration has occurred, the patient space defined by the tracking system 50, including any appropriate tracking modality (e.g. EM, optical, etc.), relative to the patient 26 is registered to the image 25. Accordingly, the points defined by the image 25 are correlated or registered to points of the patient 26. The registration allows for the tracking system 50 to track the instrument 24, transmit a tracking signal to the navigation system 20, and the navigation system 20 may then illustrate the tracked location, including position and orientation of the instrument 24, superimposed on the image 25. It is understood that processing, including executing of various program instructions, can be performed by a single processor for all of the tacking system, navigation system, imaging system, etc. Thus, the user 21 can view the display 22 and understand the position of the instrument 24 relative to the patient 26 by viewing an icon superimposed on the image 25 on the display 22 that represents the location of the instrument 24 relative to the patient 26. Thus, the instrument 24 can be navigated relative to the subject 26 with the registered image space in block 508. It is understood, however, that initial navigation is optional and need not occur for the remaining process of the flowchart 500 to occur.

The first and/or single registration can be maintained although the DRF 58 moves relative to the patient 26. The registration allows tracking of the instrument 24 or other tracked portion to be maintained and illustrated on the display 22. Thus, only a single registration may be needed although the DRF has changed configuration, including movement of the tracking device of the DRF relative to a mounting portion thereof. The tracking system 50 can track movement of the DRF to maintain the registration even though the patient moves relative to the localizer 52. Accordingly, movement of the patient 26 can be allowed during a procedure while maintaining registration and not requiring re-registration of the patient 26 to the image space of the image 25. However, during a procedure, the DRF, such as the reference arm 450 can be determined to be in an unselected or undesired position relative to the patient 26 for performing a procedure. For example, during a spinal fusion the reference arm 450 may obstruct a view or a movement of the instrument 24 for performing a procedure. Thus, the user 21 can determine or select to move the reference arm 450 relative to the clamping a fixation member 420.

Once it is determined to move the reference arm 450 relative to the clamping portion 420, the reference arm can be moved to the second position 450*b* in block 510. Generally, the reference arm 450 can be moved to a selected and known position relative to the clamping member 420 or to a determinable position relative to the clamping arm 420. Accordingly, a determined adjustment factor for movement of the reference arm can be determined and/or recalled in block 520. For example, as discussed above, the plurality of known configurations can be stored with the memory 46. Further, adjustment factors between the plurality of stored configurations can also be stored with the memory 46. Thus, determining the adjustment factor in block 520 may be recalling the adjustment factor based on an input configuration (e.g. manual, automatic, or combination of manual and automatic input)

The determination of the adjustment factor for movement of the reference arm in block 520 can be performed according to various techniques. For example, the adjustment factor is determined after the reference arm is moved to one other or a different discrete position and/or orientation relative to the clamping member 420, such as with the starburst connector 460. The determination can be made based on a manual input, an automatic input, or combinations thereof.

For example, a manual input can include the user 21 inputting into the processor system 42, using the user input 44, the new position of the reference arm 450. The new position can be related to a specific configuration of the reference arm 450 so that the adjustment factor can be determined and/or recalled. The user 21 can also input the first position 450*a* of the reference arm 450 so that the processor system 42 can determine a translation and/or rotation value of the reference arm 450. As discussed above, the adjustment factor can be stored with the memory system 46 and the adjustment factor can be recalled based on the first and second input configurations. The adjustment factor may include the translation and/or rotation value of the reference arm 450 allows the navigation system 20 to maintain the initial or only registration of the patient space to the image space. That is, the processor 42 can determine or recall the new configuration of the reference array 450, which is tracked with the tracking system 50, at the second position and/or orientation as a difference relative to the first position and/or orientation in block 504 so that the initial registration can be maintained even after movement of the reference array 450. The initial registration can be maintained as the navigation system 20 determines and/or recalls the adjustment factor based on the input or determined second position to adjust the registration based on the second position of the reference arm. The processor system 42 of the navigation system 20 can apply the adjustment factor to translate and/or rotate the difference to maintain the registration with the DRF in the second position. Again, it is understood that the reference arm of the DRF can be moved or reconfigured a plurality of times during a procedure and the registration can be maintained according to the disclosed system and method.

Alternatively, or in addition to a user inputting the different position, an automatic input of the first and/or second configuration can include a signal from a sensor that is positioned or integrated with the DRF, such as with the starburst connector 460, or other selected connector, to determine both the first configuration that can include a position and/or orientation and the second configuration that can include a position and/or orientation and automatically transfer the same to the processor system 42. Again, the processor system 42 can determine the adjustment factor that can include a translation amount and/or rotation amount to determine a difference between the first position and the second position to maintain the initial registration.

As a further example, the user 21 can touch the reference arm 450 as a selected location at the first position 450a in block 504 and the second position 450b in block 520 and the tracking system 50 can track the probe that touches the reference array 450 at both of the positions. The workstation 42 can then determine a movement amount, such as a translation and/or rotation of the reference array 450 between the two positions. The determination can, again, include a recall of the first configuration and the second configuration or difference therebetween to determine the adjustment factor to be recalled. This, therefore, can be a semi- or partially-automatic process where the user 21 need not input directly a position of the reference arm 450.

A further method can include a selected movement, such as a large scale movement, of the reference arm 450. The large scale movement can be tracked and detected by the navigation system 20. The large scale movement can be used to determine, by the processor system 42 of the navigation system 20, that the DRF is in a new configuration. The navigation system 20 can then determine the new position and then determine and/or recall the adjustment factor based thereon. This can be a substantially automatic process where the user 21 need only move the reference arm 450 and the processor system 42 determines that a movement has occurred and determines the adjustment factor. A large scale movement can be a selected movement, such as a movement of more than about 1 centimeter (cm) to about 4 cm of one of more of the tracking devices within a selected period of time, such as about 0.1 seconds to about 2 seconds. Moreover, the navigation system 20 can determine that the large scale movement is a movement of the reference arm due to the amount of movement within the selected time period. Thus, the large scale movement can be determined to not be movement of the subject 26.

It is understood, therefore, that the determination of the adjustment factor can be performed in any appropriate or selected manner between the first position of block 504 and the second position of block 510. The determined adjustment factor in block 520 can then be used to maintain registration by applying the adjustment factor (that can include a rotation and translation amount) to the registration. Generally, the adjustment factor can be used to ensure that the second position of the reference arm in block 510 is at a known position relative to the first position in block 504 so that the registration need not be performed again after movement of the reference array to a second position that is known relative to the subject fixation portion of the DRF. It is further understood that any appropriate DRF, including the various embodiments disclosed herein, can be moved from a first to a second configuration, not only the DRF 400.

After determination of the adjustment factor in block 520, an application of the adjustment factor to the registration is performed in block 530. The application of the adjustment factor in block 530 is used to maintain the registration from block in 506 as the registration in block 540. Accordingly, the registration in block 506 is maintained in block 540 due to the application of the adjustment factor for movement of the reference array. Thus, a re-registration of the patient space defined by the patient 26 relative to the image space defined by the image 25 is not required although the reference array 450, or any appropriate reference array according to various embodiments, has moved from a first position in block 504 which preceded the registration in block 506, to the second position. The first position and the second position are different, as discussed and illustrated above. The mounting portion of the DRF, however, has remained substantially fixed relative to the subject when the reference arm is in the first configuration and the second configuration.

Following the application of the adjustment factor and the maintenance of the registration in block 540, navigation of the instrument 24 can occur on block 550. Accordingly, navigation of the instrument 24 can continue, although the reference arm has moved from a first position to the second position. In particular, the registration performed in block 506 is not altered due to movement of the reference array 450, or any appropriate reference array, relative to the patient fixation portion. The registration is maintained due to the application of the adjustment factor in block 530 that is determined in block 520.

The navigation of the instrument 24 can continue with illustration of the navigated instrument superimposed on the image in block 560. The display device 22 can display an icon representing the instrument 24 superimposed on the image 25. The position of the instrument 24 can include an illustration of the entire instrument, an attachment or implant associated with the instruments 24, or any appropriate illustration. For an example, a line can be used to illustrate a central long axis of the instrument 24 without illustrating details of the instrument 24. Alternatively, or in addition thereto, a model of the instrument 24 can be superimposed on the image 25 to display substantially all of the instrument 24. Thereafter, the procedure can end at block 570. It is understood, however, that the method in flowchart 500 describes the positioning, registration, and movement of the reference arm relative to the patient 26 and does not describe and entire procedure, such as performing or completion of a procedure. Accordingly, the flowchart 500 illustrates the procedure or method of maintaining registration during movement or after movement of a reference arm of a DRF.

The DRF can be associated with a patient 26 and a first position and move to a second position in block 510 and the registration can be maintained. Thus, a procedure can be formed efficiently without requiring a re-registration of the patient relative to the image 25. This can reduce the time of a procedure and ensure proper navigation of the instrument 24. By allowing registration to occur at a single time, and registration to be maintained although the DRF has moved or an orientation of the DRF has been changed, the procedure need not stop or be slowed to re-register. Thus, a procedure can be performed in less time to allow for various benefits of the patient such as a reduced operating time, reduced or minimized anesthesia time and other various operative benefits. Further, additional image data need not be acquired of the patient 26 when a DRF has been altered, such as movement of the reference arm, to perform a second registration. By decreasing the amount of image data required, which may require ionization radiation, the subject can have limited exposure to the radiation. The known or determined position or orientation of the reference arm at the second arm relative to the first position can be used to determine the adjustment factor to retain the original registration for continuing the navigation.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A method of maintaining a registration of a subject space to an image space, the method comprising:
   accessing image data of a subject, wherein the image data defines the image space;
   generating a map between the subject space and the image space while a first tracking device is in a first position relative to a mounting portion, wherein the generated map is to form a registration of the subject space to the image space, wherein the subject defines the subject space;
   moving a probe having a second tracking device at a first time relative to the first tracking device while the first tracking device is in the first position;
   tracking at the first time the second tracking device;
   moving the first tracking device, relative to the mounting portion, from the first position to a second position after tracking at the first time the second tracking device, so as to at least one of translate or rotate the first tracking device relative to the mounting portion;
   after moving the first tracking device to the second position, moving the probe at a second time after the first time relative to the first tracking device while the first tracking device is in the second position;
   tracking at the second time the second tracking device;
   determining an adjustment factor based on tracking at the first time of the second tracking device and tracking at the second time of the second tracking device; and
   maintaining the registration of the subject space to the image space is based at least on the determined adjustment factor;
   wherein moving the probe at the second time relative to the first tracking device while the first tracking device is in the second position is to account for the moving of the first tracking device to the second position and maintain the registration in a semi-automatic manner after moving the first tracking device to the second position;
   wherein the adjustment factor includes at least one of a translation amount or a rotation amount;
   storing in the memory system the adjustment factor;
   wherein determining the adjustment factor includes recalling from the memory system the stored adjustment factor.

2. The method of claim 1, wherein determining the adjustment factor is semi-automatic.

3. The method of claim 2, wherein during the semi-automatic determination of the adjustment factor, a user does not directly input the first position of the first tracking device relative to the mounting portion or the second position of the first tracking device relative to the mounting portion.

4. The method of claim 1, further comprising:
   tracking the first tracking device at the first position; and
   tracking the first tracking device at the second position;
   wherein tracking at the first time of the second tracking device, tracking at the second time of the second tracking device, tracking the first tracking device at the first position, and tracking the first tracking device at the second position are all performed with a first tracking system.

5. The method of claim 1, further comprising:
   fixing a reference arm of a dynamic reference frame having the first tracking device at a first location and in a first orientation relative to the mounting portion when the first tracking device is in the first position; and
   fixing the reference arm, after moving the reference arm from the first location and the first orientation, at a second location and in a second orientation relative to the mounting portion when the first tracking device is in the second position.

6. The method of claim 5, further comprising mounting the dynamic reference frame to the subject with the mounting portion in a fixed position.

7. The method of claim 6, wherein the mounting portion remains fixed relative to the subject during the moving of the first tracking device from the first position to the second position.

8. The method of claim 7, further comprising:
   tracking the first tracking device.

9. The method of claim 1, further comprising:
   determining a first three-dimensional location and a first orientation of the first tracking device in the first position relative to (i) the mounting portion and (ii) the accessed image data; and
   determining a second three-dimensional location and a second orientation of the first tracking device in the second position relative to (i) the mounting portion and (ii) the accessed image data after the generating the map.

10. The method of claim 1, further comprising:
    recalling the stored adjustment factor.

11. A method of maintaining a registration of a subject space to an image space, the method comprising:
operating a dynamic reference frame having a mounting portion and an arm, wherein the mounting portion is configured to be fixed to a subject, wherein the arm is selectively moveable and fixable in a first position and a second position relative to the mounting portion;
operating a sensor positioned relative to the mounting portion;
operating an arm tracking device connected to the arm;
wherein the sensor is configured to transmit a sensor signal from the sensor to a navigation system, wherein the sensor signal is indicative of the first position of the arm and the second position of the arm;
operating a processor included with the navigation system for:
receiving the sensor signal;
based on the sensor signal,
recalling from a memory system an adjustment factor that defines a difference between the first position and the second position;
maintaining the registration of the subject space to the image space after moving the arm to the second position based at least on the recalled adjustment factor; and
storing in the memory system, prior to the operating the processor, the adjustment factor to be recalled from the memory system;
moving an instrument relative to the subject space;
tracking an instrument tracking device connected to the instrument; and
operating the navigation system to display a tracked position and orientation of the instrument relative to the image space while the arm tracking device is in the first position and while the arm tracking device is in the second position;
wherein the operating the navigation system to display is based on the registration.

12. The method of claim 11, wherein operating the sensor includes operating at least one of an encoder, a magnetic sensor, a voltage divider, a potentiometer, a counter, or a switch.

13. The method of claim 11, wherein operating the sensor includes operating at least an encoder.

14. The method of claim 11, wherein operating the sensor includes operating at least a potentiometer positioned between a first starburst portion and a second starburst portion of the dynamic reference frame.

15. The method of claim 11, wherein the sensor is integrated with the dynamic reference frame.

16. A system for maintaining a registration of a subject space to an image space, the system comprising:
a dynamic reference frame having a first tracking device and a mounting portion configured to be fixed to a subject, wherein the first tracking device is configured to be moved between at least a first configuration relative to the mounting portion and a second configuration relative to the mounting portion;
a memory system having stored thereon at least one adjustment factor including at least one of translation information or rotation information regarding a difference between the first configuration and the second configuration;
a probe configured to contact the first tracking device in the first configuration and the second configuration;
a second tracking device connected with the probe, wherein the second tracking device is configured to be tracked when the probe is contacting the first tracking device in the first configuration or the second configuration;
a processor system configured to,
form the registration of the subject space to the image space with the first tracking device of the dynamic reference frame in the first configuration,
recall the at least one adjustment factor from the memory system based on the tracked position of the second tracking device when the probe is contacting the first tracking device after the first tracking device is moved to the second configuration, and
maintain the registration of the subject space and the image space based on the recalled at least one adjustment factor.

17. The system of claim 16, further comprising:
a tracking system;
wherein the tracking system is configured to track the first tracking device and the second tracking device; and
wherein the processor system is configured to receive a tracking signal from the tracking system regarding the second tracking device when the probe is in contact with the first tracking device of the dynamic reference frame.

18. The system of claim 17, wherein the recalled at least one adjustment factor is based on the tracking signal regarding tracking the second tracking device at least at the second configuration and comprises at least one known translation information or rotational information regarding the second configuration.

19. The system of claim 16, further comprising a display device configured to display an image that defines the image space;
wherein the processor system is further configured to generate an icon superimposed on the image to represent a position and an orientation of an instrument having a third tracking device.

20. The system of claim 19, further comprising:
a first tracking system; and
a second tracking system;
wherein the first tracking system is configured to track at least the first tracking device;
wherein the second tracking system is configured to track at least one of the first tracking device, the second tracking device, or the third tracking device.

21. The system of claim 19, wherein the processor system is further configured to generate the icon superimposed on the image based on the registration that is maintained based on the recalled adjustment factor.

22. The system of claim 21, further comprising an imaging system configured to acquire image data of the subject for the image.

23. The system of claim 16, further comprising:
a sensor attached to the dynamic reference frame and configured to (i) sense at least one of a position or an orientation of the first tracking device relative to the mounting portion at the second configuration, and (ii) transmit a sensor signal to the processor system indicative of the at least one of the position or the orientation;
wherein the processor system is configured to maintain the registration based on the recalled at least one adjustment factor and the sensor signal.

* * * * *

UNITED STATES PATENT AND TRADEMARK OFFICE
CERTIFICATE OF CORRECTION

PATENT NO. : 10,531,814 B2
APPLICATION NO. : 13/950471
DATED : January 14, 2020
INVENTOR(S) : Reddy et al.

It is certified that error appears in the above-identified patent and that said Letters Patent is hereby corrected as shown below:

On the Title Page

Page 2, Line 1, Column 1, Item (56) Other Publications: Delete "Internationall" and insert --International-- therefor In the Specification Column 2, Detailed Description, Line 63: After "animal", insert --.--

Column 5, Detailed Description, Line 67: Delete "StealthStattion®" and insert --StealthStation®-- therefor Column 12, Detailed Description, Line 20: Delete "250a-d" and insert --250A-D-- therefor Column 12, Detailed Description, Line 50: Delete "222A," and insert --222a,-- therefor Column 12, Detailed Description, Line 50: Delete "222B" and insert --222b-- therefor Column 12, Detailed Description, Line 52: Delete "222A" and insert --222a-- therefor Column 12, Detailed Description, Line 54: Delete "222B" and insert --222b-- therefor Column 12, Detailed Description, Line 62: Delete "222B" and insert --222b-- therefor Column 12, Detailed Description, Line 62: Delete "222A." and insert --222a.-- therefor Column 12, Detailed Description, Line 64: Delete "222B" and insert --222b-- therefor Column 12, Detailed Description, Line 65: Delete "222A" and insert --222a-- therefor Signed and Sealed this
Nineteenth Day of May, 2020

Andrei Iancu
*Director of the United States Patent and Trademark Office*

CERTIFICATE OF CORRECTION (continued)
U.S. Pat. No. 10,531,814 B2

Column 12, Detailed Description, Line 66: Delete "222B" and insert --222b-- therefor Column 13, Detailed Description, Line 3: Delete "222B" and insert --222b-- therefor Column 14, Detailed Description, Line 25: After "assembly", delete "at"

Column 15, Detailed Description, Line 17: Delete "424" and insert --422-- therefor Column 15, Detailed Description, Line 18: Delete "422." and insert --424.-- therefor Column 15, Detailed Description, Line 64: Delete "44," and insert --46,-- therefor Column 16, Detailed Description, Line 5: Delete "array" and insert --member-- therefor Column 17, Detailed Description, Line 19: Delete "10" and insert --20-- therefor Column 17, Detailed Description, Line 44: Delete "21" and insert --26-- therefor Column 18, Detailed Description, Line 40: After "input)", insert --.--

Column 18, Detailed Description, Line 65: After "processor", insert --system--

In the Claims

Column 22, Claim 1, Line 5: After "space", delete "is"